United States Patent [19]

Pugach et al.

[11] Patent Number: 5,434,294
[45] Date of Patent: Jul. 18, 1995

[54] METHOD OF MAKING PLASTICIZERS

[75] Inventors: Joseph Pugach, Monroeville Borough; Thomas W. Smeal, Murraysville, both of Pa.

[73] Assignee: Aristech Chemical Corporation, Pittsburgh, Pa.

[21] Appl. No.: 223,399

[22] Filed: Apr. 4, 1994

[51] Int. Cl.$^6$ ............................................. C07C 67/08
[52] U.S. Cl. .................................... 560/99; 528/275; 528/279; 528/296; 528/308; 528/489; 560/78; 560/98
[58] Field of Search ............... 528/275, 279, 296, 308, 528/489; 560/78, 98, 99

[56] References Cited

U.S. PATENT DOCUMENTS

| | | | |
|---|---|---|---|
| 4,007,218 | 2/1977 | Ghanayem et al | 560/99 |
| 4,241,216 | 12/1980 | Bergman et al. | 560/99 |
| 4,284,793 | 8/1981 | Sagara et al. | 560/78 |
| 4,506,091 | 3/1985 | Deardorff | 560/99 |
| 4,526,725 | 7/1985 | Deardorff | 556/56 |
| 4,803,295 | 2/1989 | Stautzenberger et al. | 560/78 |

*Primary Examiner*—Samuel A. Acquah
*Attorney, Agent, or Firm*—William L. Krayer

[57] ABSTRACT

A process for the titanate catalyzed preparation of plasticizers from polycarboxylic acids and alcohols which minimizes waste water and is energy efficient. The reaction product is treated with aqueous caustic and is then filtered using an absorbent medium which removes titanium, caustic, acid salts and water. The need for water washing is obviated, and the final plasticizer product has excellent properties.

14 Claims, No Drawings

METHOD OF MAKING PLASTICIZERS

TECHNICAL FIELD

This invention relates to a method of making esters of aromatic and/or aliphatic polycarboxylic acids or anhydrides with alcohols containing 4–18 carbons, using organic titanates as catalysts; novelty of the process lies primarily in recovery of the product having minimal water content; this is accomplished by contacting the product with a caustic solution and passing the product containing the caustic through a multi-purpose absorbent to remove titanium, sodium and water.

BACKGROUND OF THE INVENTION

The use of alkyl titanates as catalysts for the esterification of carboxylic acids as described by Weber, U.S. Pat. No. 3,056,818 is well known. The use of titanate chelates has been described by Deardorf in U.S. Pat. No. 4,526,725. A problem with the titanate catalysts is that the titanium residues must be removed, and typically this is done by treating the crude plasticizer with aqueous caustic followed by water washing and filtration to remove metal residues. This type of processing produces large amounts of waste water which must be disposed of and is obviously undesirable.

The use of alkali for the treatment of esters prepared in the presence of titanate catalysts is described in U.S. Pat. Nos. 4,007,218 and 3,818,071.

Deardorf in U.S. Pat. No. 4,506,091 uses steam at elevated temperatures to precipitate the titanium and the residues formed are removed by filtration. The use of steam also requires care in that ester hydrolysis can occur with a concomitant rise in the acid number. While steam treatment eliminates caustic treatment, it does not address the question of waste water.

Sagara et al, U.S. Pat. No. No. 4,284,793 describe the treatment of a titanate containing plasticizer with an excess of a powdered solid base, preferably $NaHCO_3$ or $Na_2CO_3$, at temperatures in the range of 100°–200° C. This type of treatment is exemplified in that no water is added to the diester. The solid alkali is removed for further use, and activated clay added with stirring. This is followed by the addition of diatomaceous earth, and finally both treatment agents are removed by filtration to give the product. Little waste water is generated by this procedure.

While the '793 patent is an improvement over other processes, it still suffers from the need to recover and store unused solid base, and from the use of two separate treating agents after the solid base has been removed. It also does not allow for the use of water in any of the treatment steps.

SUMMARY OF THE INVENTION

Environmental considerations demand that chemical processes be more efficient and generate little if any (i.e. no appreciable amount of) waste streams. The objective of this invention is to provide an efficient plasticizer process which produces little or no waste water streams and in which metallic impurities such as titanium and sodium are removed in a safe and efficient manner.

We have discovered that aqueous caustic can be used for treating effluent from the plasticizer manufacturing process with which we work, but by careful control of the small amount of water with the caustic, and the use of certain solid absorbent media, water washing is not necessary to yield a product of excellent quality. Without water washing, the aqueous waste generated in the process is reduced far below that of conventional processes.

The method for producing a polyesterified product, hereafter called a plasticizer, according to our invention is characterized by treating the ester product obtained by reacting phthalic acid or anhydride, trimellitic acid or anhydride, or adipic acid with an alcohol having 4–18 carbon atoms in the presence of an organic titanate (such as a tetra alkyl titanate, a polymer thereof or a titanium chelate) with a small amount of an aqueous caustic solution, followed by passing the product through an absorbent medium capable of removing titanium, sodium and water from such product; we have found that fuller's earth, hydrotalcite and magnesium silicate have such capabilities.

DETAILED DESCRIPTION OF THE INVENTION

The alcohols used in the method of the present invention are those having 4–18 carbon atoms and include, for example, 2-ethylhexanol, n-butanol, isononanol, isodecanol, decanol and the like.

The esters of the present invention can be made by adding an alcohol to phthalic anhydride, trimellitic anhydride (or their corresponding acids) or adipic acid and further adding a small amount of an alkyl titanate or its polymer or a chelated titanium species and carrying out the reaction at a temperature of 180°–250° C. while stripping with an inert gas, removing formed water and reducing the acid number to 0.1 or less preferably within 2.5–6.0 hours.

The method of producing plasticizers of the present invention has the feature of adding a small amount of an aqueous solution of a caustic followed by passing through a multi-purpose absorbent medium. The aqueous caustic solution may vary in caustic concentration, but a concentration of 10–30 wt % caustic is preferred. The caustic can be any of the alkali metal hydroxides, sodium hydroxide being preferred for convenience.

The amount of caustic used should be at least equivalent to the value of the acid number of the plasticizer. The preferred amount of caustic is 1.3–1.7 times the equivalent value of the acid number of the plasticizer. Larger amount of caustic would not improve the process. Depending on the concentration of aqueous caustic an amount of 0.1–1.0 wt % caustic solution based on the total amount of plasticizer may be used. Reaction temperatures with caustic may be 80°–150° C., 90°–110° C. being preferred. A reaction time of 0.5–2.0 hours is adequate.

After the reaction with caustic is complete, the product is passed through the absorbent medium, which may be at the same temperature as the reaction with caustic. We have found that three materials are most suitable for this purpose. They are: fuller's earth, hydrotalcite and Magnesol. The latter is a synthetic magnesium silicate manufactured by the Dallas Group of America, Inc. Even though these materials are quite different chemically, their action is virtually identical. All three are efficient in complete removal of titanium, in reducing the sodium level to <1 ppm, in color enhancement, in reduction of the acid number of the plasticizer to 0.03 or less and in removal of added water. They are preferably used at levels of 2–30 g per Kg of plasticizer, with 10–15 g preferred. The use of two or three absorbent media in combination is possible, but the combination offers no advantage over their use singly. The treating agents all have the feature that they can be reused several times before their efficacy diminishes.

Thus the use of small amounts of aqueous caustic in combination with the absorbent medium leads to a plasticizer which is virtually metal free, and contains low concentrations of water. The method of this invention still allows for aqueous caustic treatment which is very efficient, but does not generate a waste water stream by requiring water washing to remove metal contaminants or excess caustic to give a plasticizer of excellent quality.

When a filter screen is used it has been found desirable to add a larger mesh material such as HyFlo Super Cel, a product of the Celite Corporation, to prevent the finer absorbent medium from passing through the screen. The larger mesh material is at best a poor absorbent medium. The filtered plasticizer is then stripped of any remaining alcohol to yield the finished product, which has excellent color and heat stability.

The characteristic feature of this invention is that there is no need to react with excessive amounts of caustic, or to steam treat, or to water wash, thus leading to a saving in energy as well as environmental benefits. The acid number of the plasticizers is superior to that obtained with more conventional processes, and the titanium content is nil with virtually no sodium. There is little, if any, waste water formed and the stability of the end product is excellent.

In the following examples, an esterification procedure was used as follows:

EXAMPLE 1

Ester of Phthalic Anhydride and 2-Ethylhexanol

To a 30-gallon oil heated autoclave equipped with a stirrer, a charging port, a gas inlet tube and an overhead system consisting of a phase separator and a condenser was added with agitation 16.3 kg of phthalic anhydride, 32.9 kg of 2-ethylhexanol and 30 g of Tyzor DEA. The latter is a titanate chelate manufactured the DuPont Chemical Corporation. $N_2$ was admitted through the gas inlet tube at a rate of 35 SCFM. The reaction mixture was heated to a maximum temperature of 228° C. during which time the water/2-ethylhexanol azeotrope was collected in the phase separator. The latter was arranged such that the 2-ethylhexanol was returned to the reactor. After 5.5 hours, the acid number had dropped to 0.085 and the reaction was terminated. The plasticizer so prepared was used for the subsequent testing at the various absorbent media.

The caustic treatment and evaluation of the multi-purpose absorbent media were carried out as follows:

1300 g of plasticizer was charged to a 2 liter flask and heated to 95° C. To this was added 0.77 g of 20 wt % NaOH and 3.25 g of distilled water, and the mixture stirred at 95° C. for 0.5 hours. The resulting mixture was divided into four portions, and each was passed sequentially through a 15.0 g pad of the multi-purpose absorbent medium to be tested. The pad of multi-purpose absorbent medium was supported on a no.41 Whatman filter paper in 3.25 inch diameter jacketed Buchner funnel. The filtrations were done at 40 mm pressure while steam was passed through the jacket of the filter funnel. The permeates were then analyzed for titanium,l sodium and water. The APHA color was determined by a standard technique, and each sample was heated to 220° C. for 2.0 hours in air. After this treatment APHA color was again determined and the clarity of the material assessed. These results are reported in Tables I and II.

Samples were freed from alcohol by stripping in a wiped film evaporator at 5 mm Hg and 130° C. The values in Table I changed little, if at all, after the stripping was completed, thus giving a plasticizer of excellent quality.

Included in Table I for comparative purposes are Hi-Flo Super Cel and Celite 512. These products are derived from diatomaceous earth. They are inferior in every regard to the preferred filtration media: fuller's earth, hydrotalcite and Magnesol (magnesium silicate).

TABLE I

Diatomaceous and Fuller's Earths as Absorbent Media for DOP

| | | Absorbent Medium | | |
|---|---|---|---|---|
| | - | Hi-Flo Super Cel | Celite 512 | Attacote LVM |
| Experiment | - | 164-171 | 164-173 | 264-163 | 164-169 |
| Filter aid, g | - | 15 | 15 | 15 | 15 |
| Pressure, mm mercury | - | 40 | 240 | 40 | 40 |
| Aliquot size, g | A- | 328 | 329 | 322 | 328 |
| | B- | 329 | 328 | 326 | 329 |
| | C- | 325 | 321 | 326 | 327 |
| | D- | 319 | 329 | 323 | 318 |
| Filtration time, | A- | 00:40 | 02:25 | 02:33 | 07:49 |
| Min:Sec | B- | 01:14 | 02:14 | 13:05 | 13:31 |
| | C- | 02:25 | 03:05 | 24:34 | 18:13 |
| | D- | 03:51 | 06:15 | 34:47 | 20:48 |
| Acid number | A- | 0.007 | 0.008 | 0.018 | 0.003 |
| | B- | 0.015 | 0.008 | 0.014 | 0.004 |
| | C- | 0.018 | 0.005 | 0.010 | 0.007 |
| | D- | 0.026 | 0.005 | 0.007 | 0.011 |
| Water content, % | A- | 0.143 | 0.243 | 0.099 | 0.150 |
| | B- | 0.104 | 0.181 | 0.074 | 0.086 |
| | C- | 0.094 | 0.177 | 0.078 | 0.085 |
| | D- | 0.085 | 0.170 | 0.076 | 0.096 |
| APHA color | A- | 25,Clear | 25,Clear | 18,ciear | 08,Clear |
| | B- | 25,Hazy | 18,Clear | 25,Clear | 08,Clear |
| | C- | 25,Clear | 18,Clear | 28,Clear | 08,Clear |
| | D- | 25,Clear | 18,Clear | 18,Clear | 08,Clear |
| Heat color | A- | 25,Lt.Floc | 35,Lt.Floc | 18,Clear | 18,Clear |
| | B- | 50,HeavyFloc | 25,Lt.Floc | 35,Clear | 18,Clear |
| | C- | 45,Lt.Floc | 35,Lt.Floc | 25,Floc | 18,Clear |
| | D- | 35,Lt.Floc | 30,Lt.Floc | 25,Floc | 18,Clear |

TABLE I-continued

Diatomaceous and Fuller's Earths as Absorbent Media for DOP

| | | Absorbent Medium | | |
|---|---|---|---|---|
| | - | Hi-Flo Super Cel | Celite 512 | Attacote LVM |
| Titanium, ppm | A- <0.40 | 0.70 | <0.40 | <0.40 |
| | B- 5.30 | 0.70 | <0.40 | <0.40 |
| | C- <0.40 | <0.40 | <0.40 | <0.40 |
| | D- <0.40 | <0.40 | <0.40 | <0.40 |
| Sodium, ppm | A- 4.90 | 7.20 | 0.27 | 0.22 |
| | B- 11.20 | 8.50 | 5.80 | 0.17 |
| | C- 2.30 | 4.70 | 9.20 | 0.22 |
| | D- 6.90 | 9.20 | 9.40 | 0.65 |

TABLE II

Magnesols and Hydrotalcites as Absorbent Media for DOP

| | | Absorbent Medium | | |
|---|---|---|---|---|
| | - | Magnesol HMR-LS | Magnesol Polysorb | Hydrotalcite |
| Experiment | - | 164-165 | 164-167 | 164-100 |
| Filter aid, % | - | 15 | 15 | 10 |
| Pressure,mm mercury | - | 40 | 40 | 40 |
| Aliquot size, g | A- | 327 | 328 | 402 |
| | B- | 325 | 327 | 400 |
| | C- | 327 | 324 | 403 |
| | D- | 323 | 321 | 384 |
| Filtration time, Min:Sec | A- | 02:59 | 02:55 | 02:00 |
| | B- | 05:29 | 07:55 | 07:00 |
| | C- | 12:02 | 13,022 | 17:00 |
| | D- | 21:16 | 16:31 | 240,00 |
| Acid number | A- | 0.003 | 0.001 | 0.019 |
| | B- | 0.003 | 0.001 | 0.026 |
| | C- | 0.004 | 0.003 | 0.028 |
| | D- | 0.012 | 0.003 | 0.034 |
| Water content, % | A- | 0.119 | 0.227 | 0.070 |
| | B- | 0.106 | 0.118 | 0.040 |
| | C- | 0.113 | 0.095 | 0.040 |
| | D- | 0.100 | 0.075 | 0.050 |
| APHA color | A- | 08,Clear | 18,Clear | 18,Clear |
| | B- | 08,Clear | 25,Clear | 18,Clear |
| | C- | 18,Clear | 18,Clear | 18,Clear |
| | D- | 18,Clear | 08,Clear | 18,Clear |
| Heat color | A- | 18,Clear | 28,Clear | 18,Clear |
| | B- | 18,Clear | 25,Clear | 18,Clear |
| | C- | 25,Clear | 25,Clear | 16,Claar |
| | D- | 18,Clear | 18,Clear | 18,Clear |
| Titanium,ppm | A- | <0.40 | <0.40 | <0.40 |
| | B- | <0.40 | <0.40 | <0.40 |
| | C- | <0.40 | <0.40 | <0.40 |
| | D- | <0.40 | <0.40 | <0.40 |
| Sodium, ppm | A- | 0.33 | 0.13 | 0.41 |
| | B- | 0.11 | 0.25 | 0.31 |
| | C- | 0.33 | 0.39 | 0.37 |
| | D- | 0.51 | 0.20 | 0.42 |

EXAMPLE 2

Trioctyl Trimellitate 192 g (1 mole) of trimellitic anhydride and 487.5 g of 2-ethylhexanol were charged to a one liter Morton flask equipped with a heating mantle, stirrer, inert gas sparge tube, sample tube and a Dean-Stark trap with a Friedrichs condenser. The air in the flask was displaced with $N_2$ after which the $N_2$ flow was cut to 100 ml/min. and heating begun with stirring. At 156° C., 0.29 g of Tyzor DEA was introduced, and heating was continued to a top temperature of 230° C. Production of water began immediately and 2 hours and 42 minutes later the acid number was 0.08 and the esterification was terminated. The pot was cooled to 95° C., and 0.60 g of 20% aqueous NaOH and 1.5 g of water were added and the batch was stirred at 95° C. for thirty minutes in order to neutralize organic acids and to hydrolyze the catalyst. The effluent was then passed through a 15 g pad of fuller's earth in a 3.25 inch diameter steam heated Buchner funnel. The permeate was stripped of excess 2-ethylhexanol on a wiped-film evaporator. After a final polishing filtration through fuller's earth, a trioctyl trimellitate product was obtained having the following properties:

Acid Number—0.04
APHA Color—25, clear
Heat Color—35, clear
Water Content—0.05%
ppm Titanium—<0.40
ppm Sodium—0.08

We claim:

1. Method of making an ester of a polycarboxylic acid whereby no appreciable amount of waste water is created, comprising (a) reacting said polycarboxylic acid or anhydride with an alkanol having 4–18 carbon atoms at a temperature of 180°–250° C. in the presence of an organic titanium-containing catalyst to obtain a plasticizer product having an acid number of no more than 0.1, (b) adding to said plasticizer product an aqueous alkaline solution at a temperature of about 80°–150° C., (c) passing said plasticizer product through an absorbent medium, thereby producing a permeate including said plasticizer product and alkanol and having reduced titanium and sodium contents, (d) stripping alkanol from said permeate, and (e) recovering said plasticizer product therefrom.

2. Method of claim 1 wherein the amount of aqueous alkaline solution added in step (b) is at least equivalent to the acid number of said polyesterified product.

3. Method of claim 1 wherein the aqueous alkaline solution added in step (b) is equivalent to about 1.3 to about 1.7 times the acid number of said polyesterified product.

4. Method of claim 1 wherein the aqueous alkaline solution comprises sodium hydroxide.

5. Method of claim 1 wherein the temperature in step (b) is about 90°–110° C.

6. Method of claim 1 wherein the absorbent medium is fuller's earth.

7. Method of claim 1 wherein the absorbent medium is hydrotalcite.

8. Method of claim 1 wherein the absorbent medium is magnesium silicate.

9. Method of claim 6 wherein the fuller's earth is used in an amount about 2–30 g fuller's earth per kilogram of plasticizer product.

10. Method of claim 1 wherein the polycarboxylic acid or anhydride is phthalic anhydride.

11. Method of claim 1 wherein the alcohol is 2-ethylhexanol.

12. Method of claim 1 wherein the polycarboxylic acid or anhydride is trimellitic anhydride.

13. Method of making an ester of a polycarboxylic acid comprising (a) reacting said polycarboxylic acid or anhydride with an alkanol having 4–18 carbon atoms at a temperature of 180°–250° C. in the presence of an organic titanium-containing catalyst to obtain a plasticizer product having an acid number of no more than 0.1, (b) adding to said plasticizer product an aqueous alkaline solution at a temperature of about 80°–150° C., (c) passing said plasticizer product through an absorbent medium selected from the group consisting of fuller's earth, hydrotalcite, and magnesium silicate, thereby producing a permeate including said plasticizer product and alkanol and having reduced titanium, sodium and water contents, (d) stripping alkanol from said permeate, and (e) recovering said plasticizer product therefrom.

14. Method of claim 1 wherein said aqueous alkaline solution has a caustic concentration of 10–30 wt %.

* * * * *